(12) United States Patent
Cross

(10) Patent No.: US 10,959,620 B1
(45) Date of Patent: Mar. 30, 2021

(54) SYSTEM AND METHOD OF IN VIVO TESTING FOR RECENTLY VIABLE DENTAL CELLULAR DEBRIS

(71) Applicant: Randolph Cross, Aptos, CA (US)

(72) Inventor: Randolph Cross, Aptos, CA (US)

( * ) Notice: Subject to any disclaimer, the term of this patent is extended or adjusted under 35 U.S.C. 154(b) by 0 days.

(21) Appl. No.: 16/881,266

(22) Filed: May 22, 2020

Related U.S. Application Data

(60) Provisional application No. 63/000,251, filed on Mar. 26, 2020.

(51) Int. Cl.
*A61B 5/00* (2006.01)
*A61K 49/00* (2006.01)
*A61C 5/40* (2017.01)

(52) U.S. Cl.
CPC .......... *A61B 5/0088* (2013.01); *A61B 5/0071* (2013.01); *A61C 5/40* (2017.02); *A61K 49/0052* (2013.01)

(58) Field of Classification Search
None
See application file for complete search history.

(56) References Cited

U.S. PATENT DOCUMENTS 9,427,384 B2 *  8/2016  Kutsch ..................... A61K 8/21

OTHER PUBLICATIONS

UltraSnap product information (Hygenia company, 2019). (Year: 2019).*
Tan et al (J Endodontics, 41:447-450, 2015) (Year: 2015).*
BacTiter—Glo Microbial Cell Viability Assay Technical Bulletin (Promega, 2019). (Year: 2019).*

* cited by examiner

*Primary Examiner* — Brian Gangle
(74) *Attorney, Agent, or Firm* — Pharar Patents & Intellectual Property; Andrew A. Pharar

(57) ABSTRACT

A system and method of in vivo testing for recently viable dental cellular debris is disclosed herein. The present invention discloses a method and apparatus for detecting for the presence of cellular debris from an endodontic cavity and other areas of a tooth by testing for the presence of cellular debris such as Adenosine Triphosphate (ATP). The sample is collected from a tooth or endodontic cavity and combined with a chemical indicator which causes a detectable change in the indicator that is sensed by a luminescence reader. The level of ATP in a sample corresponds to the level of contamination still present in the tooth or endodontic cavity and can be used to determine what additional steps, if any, are necessary in order to clean and disinfect the tooth. This method of sampling the tooth or endodontic cavity allows for a rapid, chair-side, affordable, and easy to use method to determine the level of cellular contamination.

13 Claims, 4 Drawing Sheets

SYSTEM AND METHOD OF IN VIVO TESTING FOR RECENTLY VIABLE DENTAL CELLULAR DEBRIS

TECHNICAL FIELD OF THE INVENTION

The present invention relates in general to dental treatment methods, and, more specifically, to a system and method of in vivo testing for recently viable dental cellular debris.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

The dental pulp is contained within a tooth and may become injured for variety of reasons including physical trauma, microbial contamination, and chemical trauma that may result in the tooth undergoing an inflammatory and often infectious process that results in damage to the tooth and its supporting structures. A root canal procedure is a way of reducing and ideally eliminating the inflammatory and infectious process inside a tooth to allow for healing in the structures surrounding the tooth. A root canal procedure consists of the removal of dental pulpal tissue and removal of microorganisms from inside of the root canal. The root canal is then filled with various materials to seal off any remaining microorganisms or pulp tissue within the endodontic cavity to prevent reinfection of the root canal space and to prevent inflammatory signals from escaping the root canal. After a root canal procedure is complete the root canal is sealed with a filling material or covered with a crown in order to restore function to the tooth and prevent reinfection of the root canal.

A root canal procedure typically involves a dentist opening the tooth with a dental drill through the crown of the tooth in order to gain access to the dental pulp. The dentist will then remove the dental pulp and microorganisms mechanically by enlarging the root canal using various metal files. Disinfection of the tooth and endodontic cavity can also be aided chemically with various rinses, solutions, and other methods that remove additional pulpal tissue and microorganisms not removed by the mechanical instruments. A dentist may also schedule additional visits to further reduce the number of vital microorganisms that may be present in a root canal.

Tissue debris, microorganism debris, and viable microorganisms left in the root canal after completion of the root canal procedure can result in a failed root canal procedure in which the patient continues to show radiographic bone loss around the tooth and experience possible symptoms such as pain or swelling. Because there is currently no easy way to test for the level of cellular debris in a tooth, dental practitioners may end up unnecessarily removing more root canal structure then necessary to prevent the chances of reinfection. Even after enlarging the root canal to larger sizes by mechanical instrumentation the endodontic cavity may still contain high levels of cellular debris.

Much research has been conducted into the effect of various factors on the success of root canal procedures. One study demonstrated that only 58.8% of the root canal walls are touched by the root canal rotary files, which means that 41.2% of the root canal walls are untouched and depend on chemical irrigation to clean and disinfect the tooth. Even with all the mechanical instruments, chemical disinfectants, and various ways of activating those disinfectants approximately 15-25% of root canal procedures fail.

Other research has shown that cellular contamination plays a major role in the success rates of endodontic procedures. A related study showed that a root canal procedure that cultures negative for bacteria just prior to sealing the root canal has a 94% success rate compared to a success rate of only 68% for root canal procedures that culture positive for bacteria just prior to sealing the root canal.

While the goal of a root canal procedure is to seal off those remaining areas that contain cellular debris with a filling material, the filling and sealing materials have thus far failed clinically to provide a perfect seal of the tooth, especially when difficult anatomy and lateral canals are present. Given the large number of root canal procedures completed every year in the United States, the importance of cellular contamination in the outcome of those root canal procedures, and the difficulties that currently exist when filling a root canal, there remains a need for a rapid and quantitative method of testing for the level of cellular contamination inside of a root canal.

There are several patents and research studies that relate to the field of endodontic bacterial contamination and imaging.

U.S. Pat. No. 9,611,500 describes a method of testing for the presence of viable cellular tissue within a root canal by incubating a sample of the root canal with an inactive form of a fluorescent dye that is activated in the presence of viable cells to emit fluorescence. However, the device requires that the cells be viable in order to test for the presence of cellular debris, which limits the sensitivity of the device because inactive, dormant, or non-viable cells that do use the specific viable cellular substrate to create the fluorescent dye are not detected. Also, the device requires that the cells are incubated for a given period of time which results in additional delays for the dentist and the patient while they wait for the results of the viability test.

United States Patent Application 2003/0108490A1 describes a method of testing for the presence of periapical disease or inflammation by testing for the level of matrix metalloproteinases in the periapical exudate. The method uses matrix metalloprotease antibodies and fluorescent dyes to test for the presence of inflammation that is leaking into the root canal system from periapical tissues. The test does not check for the presence of contamination that remains in the root canal system and does not measure cellular debris, but rather measures for the presence of inflammatory indicators.

U.S. Pat. No. 9,427,384 describes a method of determining a patient's caries risk through a patient questionnaire and using an Adenosine Triphosphate (ATP) Bioluminescence sampler to test for the presence of ATP on the outside surface of a tooth. Depending on the results of the questionnaire and the ATP test the patient is recommended various oral rinses to reduce their risk of caries. This method of tooth biofilm testing does not give the dentist any insight into the contamination within the tooth or root canal, though. The oral rinse treatment protocol recommended for these patents is meant to reduce the patient's biofilm and bacteria levels on the tooth surface and outside of the tooth, but is not intended to reduce microorganisms inside of the tooth or root canal system.

U.S. Pat. No. 9,562,253 describes a method of using a reagent to lyse cells of bacteria, and then using an ATP colorimetric agent to observe for a change in color with the unaided eye when bacteria is present beyond a given concentration in the sample. By determining if bacterial ATP is present the practitioner is aided in deciding if the patient has a bacterial infection, as opposed to a viral infection or other inflammatory condition. Bacterial testing in endodontics to determine the cause of infection is of little use, though, as virtually all infected root canals contain some bacteria. Also, this method of determining the presence of bacteria in a sample requires subjective interpretation of the test color change, which is not objectively quantitative or sensitive enough to be used in an endodontic setting.

Other research has attempted to quantify the bacterial contamination in a root canal, but the suggested protocol was complicated and never caught on with dental practitioners. The protocol required materials and techniques not commonly used by dental practitioners, such as using 96 well plates, serial dilutions, a centrifuge, pipettes to measure the reagent, and known concentrations of bacterial cultures. The procedure also required five minutes to obtain results, which is an extended period of time for the patient and the dental practitioner to wait, especially if multiple tests are needed. Due to the complicated protocol, need for additional laboratory equipment, and the length of time needed to obtain results the method of same day bacterial testing is not used.

Thus, there is a need in the art for a system and method of in vivo testing for recently viable dental cellular debris that provides a dental practitioner with accurate and reliable measures of the bacterial load within a root canal during or prior to completing the root canal procedure. Such a system and method may further increase the success rate of root canal procedures so as to improve patient outcomes and reduce the need for corrective follow-up procedures. It is to these ends that the present invention has been developed.

BRIEF SUMMARY OF THE INVENTION

To minimize the limitations in the prior art, and to minimize other limitations that will be apparent upon reading and understanding the present specification, the present invention describes a system and method of in vivo testing for recently viable dental cellular debris.

It is an objective of the present invention to provide a system and method of in vivo testing for recently viable dental cellular debris that may comprise a rapid, simple, and cost-efficient test to determine the level of cellular debris present in an endodontic cavity.

It is another objective of the present invention to provide a system and method of in vivo testing for recently viable dental cellular debris that may comprise a rapid, simple test to determine the level of cellular debris present in an endodontic exudate.

It is another objective of the present invention to provide a system and method of in vivo testing for recently viable dental cellular debris that may comprise a rapid, simple test to determine the level of cellular debris present in a tooth.

It is another objective of the present invention to provide a system and method of in vivo testing for recently viable dental cellular debris that may comprise a rapid, simple test to determine the level of cellular debris present in a dental restorative sample.

It is another objective of the present invention to provide a system and method of in vivo testing for recently viable dental cellular debris that may comprise a luminescence sampler and luminometer used to determine the level of cellular debris that remains within a sample.

It is another objective of the present invention to provide a system and method of in vivo testing for recently viable dental cellular debris that may be used to determine the level of treatment that is needed to disinfect a tooth while minimizing unnecessary treatments and unnecessary removal of healthy tooth structure.

It is another objective of the present invention to provide a system and method of in vivo testing for recently viable dental cellular debris that may comprise a translucent storage well for detecting for the presence of luminescence in a sample.

It is another objective of the present invention to provide a system and method of in vivo testing for recently viable dental cellular debris that may comprise lysing solutions to increase the concentration of free cellular debris present in a sample.

It is another objective of the present invention to provide a system and method of in vivo testing for recently viable dental cellular debris that may comprise buffering solutions to buffer the solution from tooth disinfecting solutions that may be in trace concentrations in the samples.

It is another objective of the present invention to provide a system and method of in vivo testing for recently viable dental cellular debris that may comprise a luminometer that reports results, usually as Relative Light Units (RLUs).

It is another objective of the present invention to provide a system and method of in vivo testing for recently viable dental cellular debris that may comprise luminescent chemical indicators to test for cellular contamination.

It is another objective of the present invention to provide a system and method of in vivo testing for recently viable dental cellular debris that may comprise a test for the presence of adenosine triphosphate (ATP).

It is another objective of the present invention to provide a system and method of in vivo testing for recently viable dental cellular debris that may comprise a test for the presence of adenosine diphosphate (ADP).

It is another objective of the present invention to provide a system and method of in vivo testing for recently viable dental cellular debris that may comprise a test for the presence of adenosine monophosphate (AMP).

It is another objective of the present invention to provide a system and method of in vivo testing for recently viable dental cellular debris that may comprise a luciferase enzyme.

It is another objective of the present invention to provide a system and method of in vivo testing for recently viable dental cellular debris that may comprise a recombinant luciferase enzyme.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

DETAILED DESCRIPTION OF THE INVENTION

Figure 1:
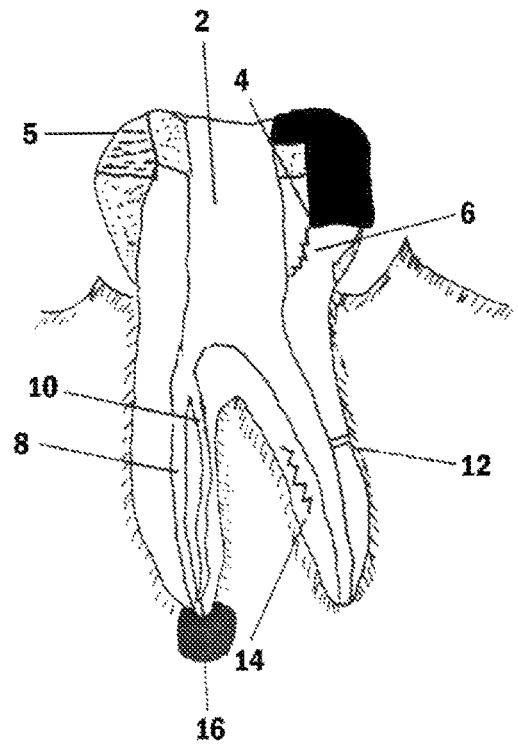
FIG. 1 illustrates a longitudinal cross-sectional view of a tooth receiving an endodontic therapy that has a dental restoration, a dental crack, and a vertical root fracture.

Certain terminology is used in the following description for reference only and is not limiting. The words "front," "rear," "anterior," "posterior," "lateral," "medial," "upper," "lower," "outer," "inner," and "interior" refer to directions toward and away from, respectively, the geometric center of the invention, and designated parts thereof, in accordance with the present disclosure. Unless specifically set forth herein, the terms "a," "an," and "the" are not limited to one element, but instead should be read as meaning "at least one." The terminology includes the words noted above, derivatives thereof, and words of similar import.

The system and method of in vivo testing for recently viable dental cellular debris allows for a rapid, simple test to determine the level of cellular debris present in an endodontic cavity, endodontic exudate, tooth, or other dental restorative samples. Testing of a sample with a luminescence sampler and luminometer is used to determine the level of cellular debris that remains within the sample, and can be used to determine the level of treatment that is needed to disinfect the tooth while minimizing unnecessary treatments and unnecessary removal of healthy tooth structure. Using a luminescent sampler and a luminometer is a simple, fast, cost effective, accurate, and quantitative way to test for cellular debris in a sample.

A translucent storage well is used when detecting for the presence of luminescence in a sample. Lysing solutions may be used to increase the concentration of free cellular debris present in the sample. Buffering solutions may also be used in order to buffer the solution from tooth disinfecting solutions that may be in trace concentrations in the samples. To more quantitatively measure the level of luminescence present in a sample a luminometer may be used, and the results are typically given as Relative Light Units (RLUs).

Several luminescent chemical indicators may be used to test for cellular contamination, but one embodiment of the system and method of in vivo testing for recently viable dental cellular debris is to test for the presence of nucleotides or phosphorylated nucleotides such as adenosine triphosphate (ATP), adenosine diphosphate (ADP), and adenosine monophosphate (AMP). By testing for the presence of nucleotides and phosphorylated nucleotides the dental practitioner can have a good idea as to the level of cellular contamination in the sample due to the ubiquitous nature of those compounds in cellular debris.

In another embodiment of the system and method of in vivo testing for recently viable dental cellular debris, the samples can be tested for the presence of ATP as the presence of ATP indicates the presence of viable and recently viable cellular debris in the sample. One method to test for the presence of ATP uses a luciferase or a recombinant luciferase enzyme, but other enzymes that undergo luminescence in the presence of cellular debris may be used. Commonly used luciferase enzymes, which may be known as glow enzymes, have a half-life of about thirty to sixty minutes. The use of a fast-acting luciferase enzyme, which may be known as a flash enzyme, would allow a luminescence change to be observed in less than five minutes. Luminescence samplers offer a convenient way to test for cellular debris in a sample as the solutions required for the test are already present in the sampler.

While the ideal embodiment of the system and method of in vivo testing for recently viable dental cellular debris is to use the luminescent sampler to test the samples immediately for the presence of cellular debris such as ATP, there are times when the dental practitioner may want to determine the presence of viable cells in a sample. When the dental practitioner would like to determine the presence or quantity of viable cells present in a sample the dental practitioner can place the endodontic or dental sample in a specific growth medium lacking in certain organic elements for a predetermined period of time and then test for the presence or quantity of specific organic elements after an incubation period. An increase in those specific organic elements would signify that viable cells are present, as well as provide an estimated concentration of viable cells in the original sample.

The illustrations of FIGS. 1-9 illustrate various aspects of a system and method of in vivo testing for recently viable dental cellular debris, as contemplated by the present disclosure. The invention deals with testing for cellular contamination inside of a tooth, which is accomplished by obtaining a sample from the tooth or endodontic cavity, combining the sample with a luminescent chemical indicator that has a measurable change in the presence of cellular debris, and measuring the presence and amount of luminescence created by the sample. Ideally a device such as a luminometer is used to more accurately determine the presence and intensity of luminescence from the solution.

Some of the possible applications of the invention include, but are not limited to: a quantitative way to determine if an endodontic space is sufficiently clean, a way to test for microbial contamination around a dental restoration, a quantitative way to test the tooth surface for the presence of caries, a quantitative way to evaluate cellular contamination at the tooth restoration margin, a method for testing for leaking restorations, a method to detect for missed canals and other uncleaned anatomy, a way to detect for cracks, or a way to detect a root fracture.

The illustration of FIG. 1 depicts a tooth that has been opened and needs endodontic therapy. The tooth depicts several of the possible locations, any of which may be considered a dental site, that the invention may be used to test for contamination. Such a sample may be known as an in vivo debris sample, and may or may not contain viable, recently viable, or non-viable cellular debris. As contemplated by the present invention, the in vivo debris sample may contain nucleotides such as, for example, adenosine triphosphate, adenosine diphosphate, adenosine monophosphate, deoxyribonucleic acid, or other similar nucleotides, which may trigger a luminescence change when combined with a luminescent cellular debris indicator. The degree of change in luminescence based on the concentration of such nucleotides may be measured to indicate a cellularity concentration indicating the presence of bacterial, viral, or other infectious material in the dental site.

By testing the pulp chamber 2 of the tooth for contamination it gives the dental practitioner an idea as to the level of cellular contamination that is present in the tooth. By taking samples of the pulp chamber 2 before or during root canal treatment the dental practitioner can know what additional steps, if any, are needed to disinfect the tooth to complete treatment.

Sampling of the pulp chamber 2 may also be done after root canal treatment to test for leakage of any restorative materials that may be above the endodontic cavity such as fillings 4, crowns, or other restorative materials to determine if those fillings 4 or crowns are still functional or if they need to be replaced. Sampling of caries lesions 5 is also useful for the dental practitioner as knowing the level of contamination in the tooth can aid the practitioner to know when to stop removing infected tooth structure. Sampling of tooth material is especially important when the infected tooth is close to the dental pulp and the practitioner must decide if they should remove more tooth structure and risk entering the pulp or if the infected tooth structure is sufficiently clean that they can place the restorative material. Sampling of cellular debris can also be useful on the tooth surface or tooth replacing dental material as the presence of cellular debris signifies that the tooth or dental material may need additional dental treatments or that the tooth or structure may need to be replaced.

Cellular debris testing may also be useful when determining the extent of a crack 6 that may form in a tooth. By testing for cellular contamination that is present in a tooth with a crack 6 it can aid the dental practitioner in determining the long-term prognosis of the tooth. Cellular contamination testing can also be useful inside of the root canal 8 to determine if the root canal 8 is sufficiently clean or if additional treatments, such as mechanical enlargement, mechanical cleaning, chemical agents, medicated substances, additional irrigation, or other treatments, such as additional visits, are needed to sufficiently disinfect the root canal. Cellular sampling of the root canal can also be used to test for missed canals 10, lateral canals 12, and vertical root fractures 14 as these areas may result in higher levels of cellular debris inside an otherwise cleaned root canal. Dental practitioners can also test the level of cellular debris in the exudate 16 to help determine if additional treatments, visits, or surgeries are needed to treat the tooth.

Figure 2:
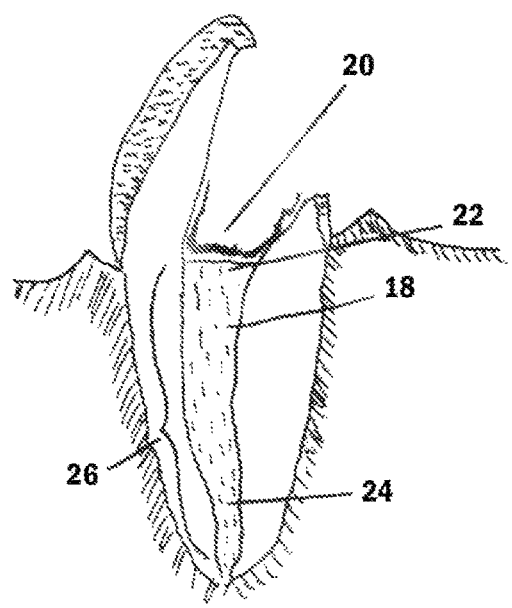
FIG. 2 illustrates a longitudinal cross-sectional view of a tooth that has a previous root canal treatment and has been exposed to the oral environment.

The illustration of FIG. 2 is a longitudinal cross section of a tooth that has had a previous root therapy which is filled with a root filling material 18, but has been exposed to the oral environment and now has a biofilm covering the root canal and internal tooth surfaces 20. By testing the top surface portion 22 of the filling material 18 the dental practitioner can better determine if the filling is contamination and what additional treatments, if any, are needed to remove the cellular debris. By comparing the level of cellular contamination in the apical 24, mid root, and coronal areas of the root canal the practitioner can better diagnose pathologies such as coronal leakage, apical leakage, vertical root fracture, infected lateral canals, extra radicular infections, and other pathologies. Testing of the endodontic cavity 26 is also useful in retreatment cases as it can aid the dental practitioner in deciding what additional steps, or additional visits, are necessary to sufficiently decontaminate the root canal.

Figure 3:
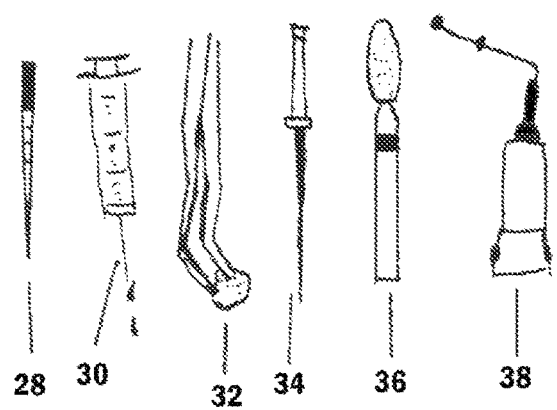
FIG. 3 illustrates a front view of several methods of transferring the sample from the tooth or endodontic space to the luminescence sampler.

The illustration of FIG. 3 depicts some of the methods that a dental practitioner can use to collect dental and endodontic samples that are to be tested for cellular contamination. A paper point 28 can be placed inside of the endodontic chamber to absorb a sample from an endodontic chamber. A sample from the tooth or endodontic cavity can be aspirated into a holding well or syringe 30. A cotton pellet or other absorbent material 32 that has been placed in the tooth, or scrubbed on the surface of an area of interest, can be used to extract a sample from the tooth or endodontic cavity. Debris from an endodontic cleaning instrument 34 or dental drill and tooth scraping device 36 can also sampled for cellular contamination. Previous endodontic filling materials may also be tested for cellular contamination by using instruments such as a heated plugger 38 to remove the previous filling material which can then be tested for cellular contamination.

Figure 4:
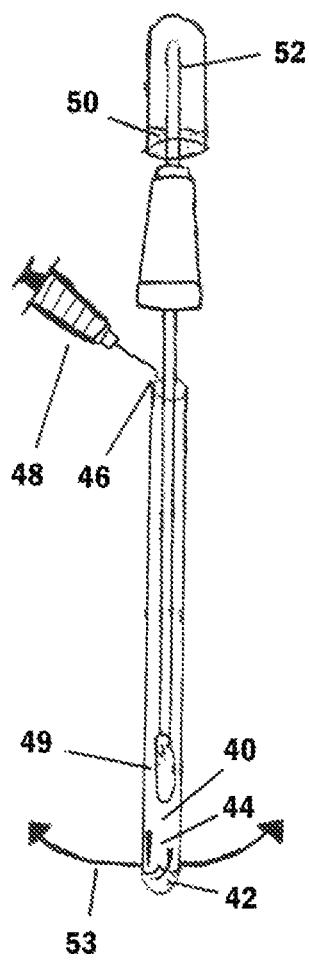
FIG. 4 illustrates an overall view of an exemplary luminescence sampler.

The illustration of FIG. 4 depicts one embodiment of a luminescence sampler. The luminescence sampler may have a translucent storage well 40 for the solutions. A buffering agent 42 may also be present to buffer the solution from any chemicals or pH changes that may be present in the sample. Cell lysing agents 42 and organic debris freeing solutions may also be present to free additional organic compounds from the sample.

FIG. 4 also depicts paper points in the bottom of the storage well 44 in addition to a liquid sample 46 being injected into the well from a syringe 48. Here the luminescence sampler contains a swab that can either be used to test surfaces for cellular contamination, but in FIG. 4 the swab is instead used to push testing samples into the bottom of the clear storage wells 49. While this luminesce sampler depicts a swab, in other samplers it may take other forms, or be missing entirely. A premeasured amount of chemical indicator 50 is also present in the luminescence sampler and in this device the top of the device 52 can be bent and squeezed to release the chemical indicator into the storage well.

Such storage wells 44 may comprise mobile test containers and may further contain prepared combinations of luminescent cellular debris indicators, luciferase enzymes, extracting agents, lysing agents, buffering agents, and other appropriate compounds. Other devices may require twisting, squeezing, taping, or other methods to release the chemical indicator into the storage well 44. Gentle agitation 53 is then used to mix the samples before testing in a luminometer. In some embodiments the storage wells 44 may be disposable.

Figure 5:
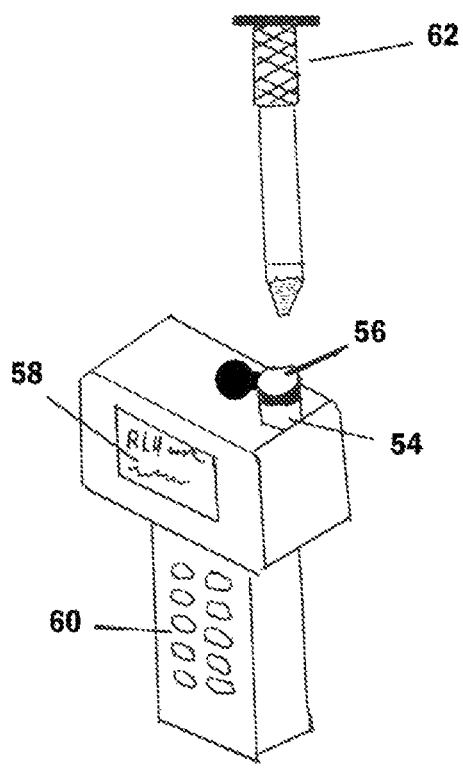
FIG. 5 illustrates a side view of an exemplary luminometer single-tube reader.

The illustration of FIG. 5 depicts one embodiment of a luminometer with an area to insert the luminescent sample 54 and a cover 56 that can be closed to prevent background light from entering the luminometer. The luminometer typically has a screen 58 to view the results of the test and a way to adjust the settings 60. This luminometer demonstrates a different method of releasing the chemical indicator into the testing sample in which the luminescence sampler 62 is twisted instead of bent like the luminometer in FIG. 4.

Figure 6:
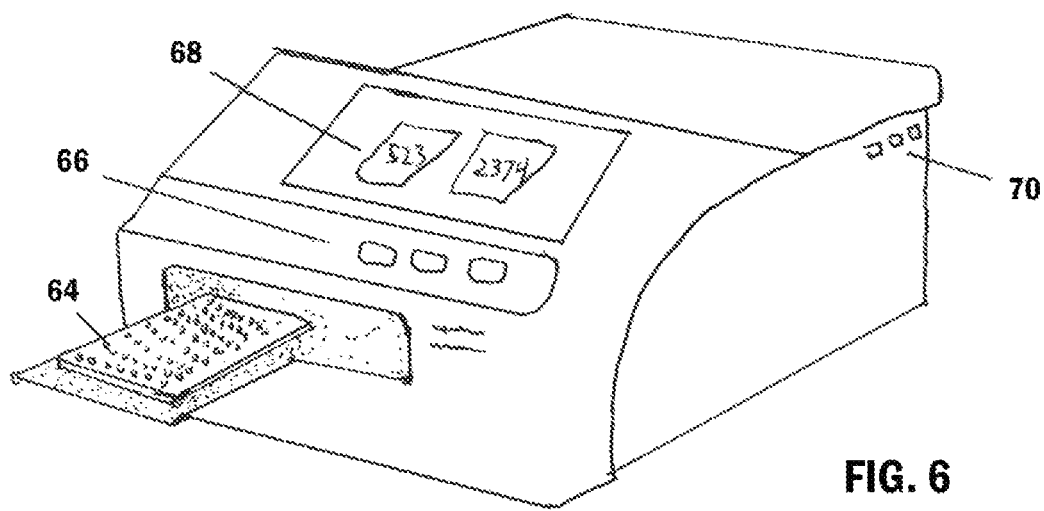
FIG. 6 illustrates a front view of an exemplary luminometer microplate reader.

The illustration of FIG. 6 is an alternative embodiment of the luminometer where the chemical indicator is being added to translucent storage wells like a microplate 64 or a test tube. The luminometer also has a way to adjust the settings 66, read the results 68, and may also have a way to import that data 70.

Figure 7:
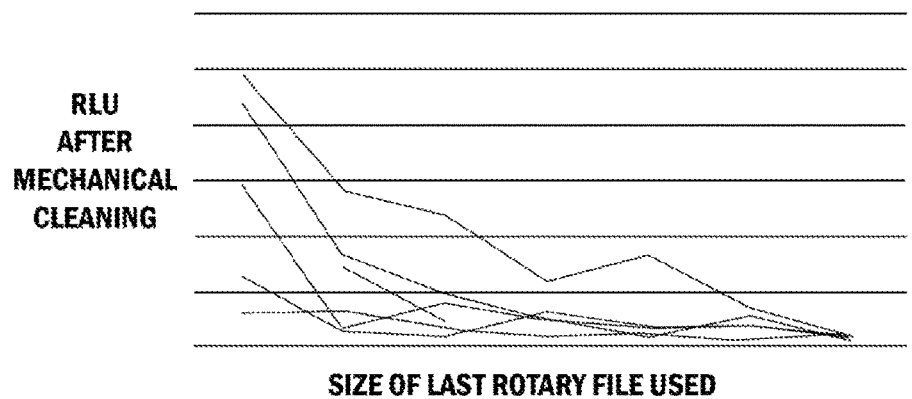
FIG. 7 graphically presents the RLU results of various samples from several extracted teeth that have been cleaned with progressively larger instruments.

The illustration of FIG. 7 is a graph of the RLU's from endodontic samples taken from extracted teeth. Initially small stainless-steel hand files were used to enter the root canal, then endodontic rotary files were used to further clean the root canal. Samples were transferred from the tooth to a luminescent sampler using between one to three paper points. For this test the Ultrasnap Bioluminescence sampler and the Hygiena SystemSure Plus ATP Luminometer were used to determine the level of ATP present in the sample, but other luminometers and luminescence samplers could have been used. As the teeth were cleaned with progressively larger instruments there was a trend for decreased RLU's, which correlates to less cellular debris inside of the tooth. The rate of decontamination varied between teeth and this test suggests by testing for the RLU's during a dental procedure a dentist can better tailor the tooth's treatment to the level of contamination present in the sample.

Figure 8:
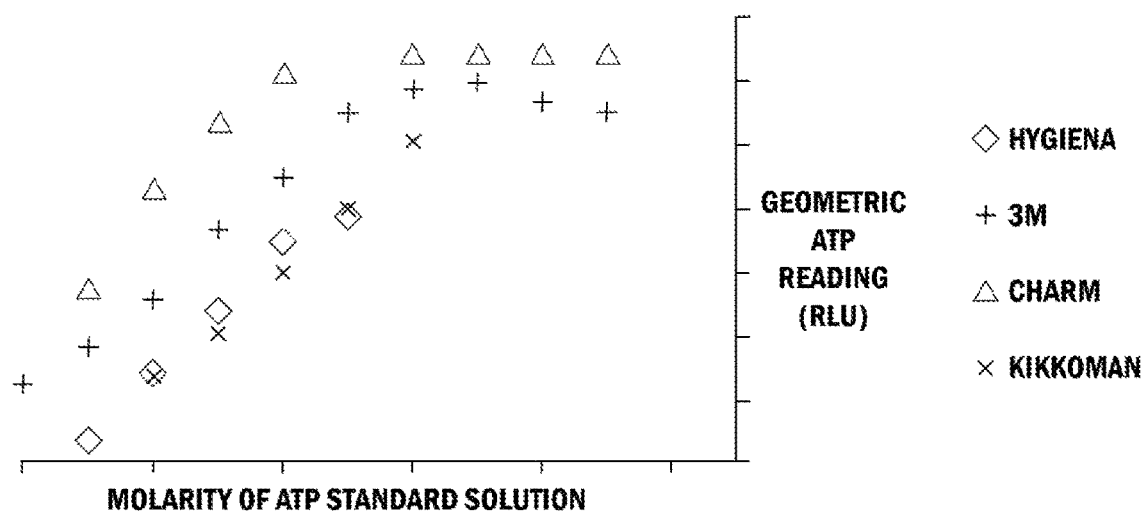
FIG. 8 graphically presents the RLU results of the luminometer compared to the ATP levels of various luminescent samplers and luminometers.

The illustration of FIG. 8 is a graph comparing the RLU's of various luminometers to various concentrations of ATP. By testing the endodontic or tooth sample for cellular debris such as ATP the dental practitioner can determine the amount of cellular debris in the sample and compare the level of cellular debris to known RLU's from known concentrations of viable bacteria.

Figure 9:
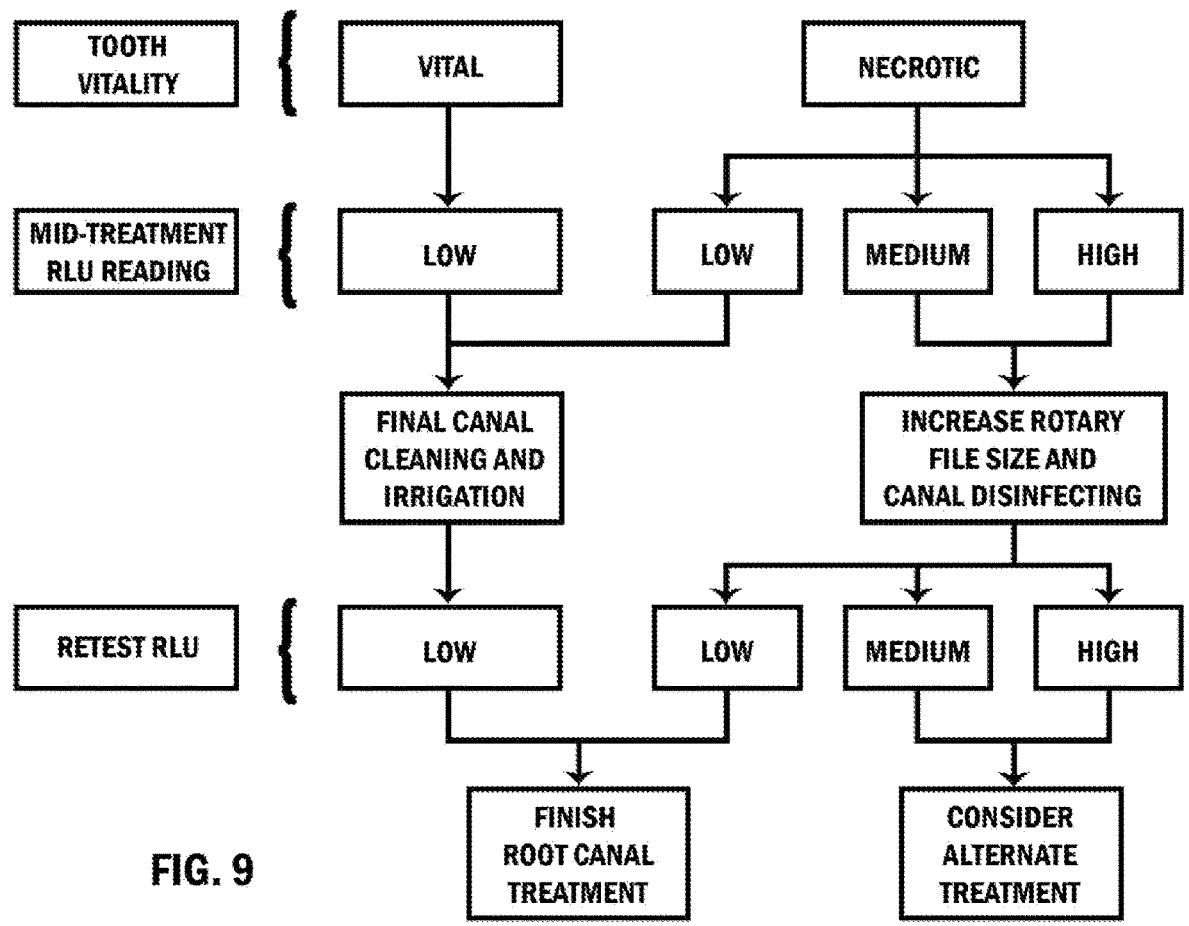
FIG. 9 schematically presents a flow chart of decision processes of a system and method of in vivo testing for recently viable dental cellular debris.

The illustration of FIG. 9 is a diagram of a decision tree that can be used by the dental practitioner along with the RLU of an endodontic sample to decide what additional cleaning and disinfecting steps are necessary to reduce the contamination levels to an acceptable level. The decision tree relies primarily on the tooth vitality and corresponding RLU indication measured. A medium or high RLU indication, suggesting a medium or high concentration of bacterial, viral, or other infectious material in the dental site, may indicate the need for further treatment of the dental site to effectively complete the dental procedure and reduce the need for follow-up treatments.

While the invention has been described in connection with what is presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

I claim:

1. A method of in vivo testing for viable dental cellular debris, comprising:
   sampling an endodontic cavity during a root canal procedure to acquire an endodontic sample;
   combining said endodontic sample with a luminescent cellular debris indicator;
   observing a combination of said endodontic sample and said luminescent cellular debris indicator for a luminescence change indication; and
   measuring said luminescence change indication to determine a presence of cellular debris;
   wherein said luminescent cellular debris indicator changes luminescence in the presence of a phosphorylated nucleotide;
   wherein said luminescent cellular debris indicator does not change luminescence in the absence of said phosphorylated nucleotide;
   wherein an intensity of said luminescence increases with an increase in said presence of cellular debris;
   wherein said luminescence change indication is caused by a luciferin-luciferase reaction facilitated by using a luciferase enzyme; and
   wherein said luciferin-luciferase reaction is completed and said presence of cellular debris is determined in less than a five-minute time period.

2. The method of claim 1,
   wherein said presence of cellular debris is used to determine a treatment protocol for treating said endodontic cavity; and
   treating said endodontic cavity according to said treatment protocol.

3. The method of claim 2,
   wherein said measuring of said luminescence change indication is performed by a luminometer; and
   wherein said luminometer indicates to a user said presence of cellular debris.

4. The method of claim 3,
   wherein said combining of said endodontic sample with said luminescent cellular debris indicator is performed in a mobile test container; and
   wherein said mobile test container is translucent.

5. The method of claim 3,
   wherein said combining of said endodontic sample with said luminescent cellular debris indicator further includes an extracting agent; and
   wherein said extracting agent separates said nucleotide content from said endodontic sample.

6. The method of claim 3,
   wherein said combining of said endodontic sample with said luminescent cellular debris indicator further includes a buffering solution; and
   wherein said buffering solution maintains said luciferin-luciferase reaction.

7. The method of claim 4,
   wherein said mobile test container is a disposable luminescent sampler containing a plurality of premeasured solutions to test for said presence of cellular debris.

8. The method of claim 4,
   wherein said mobile test container is a single-well container.

9. The method of claim 4,
   wherein said luminescence change indication is caused by said luciferin-luciferase reaction facilitated by using a flash-type kinetics of said luciferase enzyme.

10. The method of claim 4,
    wherein said luminometer indicates to said user said presence of cellular debris on a scale of relative light units.

11. The method of claim 4,
    wherein said presence of cellular debris is compared with a plurality of known pathological samples to determine said treatment protocol.

12. The method of claim 4,
    wherein sampling said endodontic cavity during said root canal procedure to acquire said endodontic sample does not require an enlarging of said endodontic cavity.

13. The method of claim 4,
    wherein said endodontic cavity is selected from the group consisting of a tooth root, a material filling inside of said tooth root, a tooth pulp chamber, and a material inside of said tooth pulp chamber.

* * * * *